United States Patent [19]
Zinnecker

[11] Patent Number: 5,035,248
[45] Date of Patent: Jul. 30, 1991

[54] POLYOLEFIN SHEATH AND SILICONE O-RING FOR MEDICAL INSTRUMENT

[76] Inventor: Hal P. Zinnecker, 8 Belleview Blvd., Belleair, Fla.

[21] Appl. No.: 41,430

[22] Filed: Apr. 23, 1987

[51] Int. Cl.⁵ ............................................. A61B 17/32
[52] U.S. Cl. .................................... 128/751; 606/205
[58] Field of Search ................... 128/321, 303.15, 751, 128/305, 752; 606/205

[56] References Cited

U.S. PATENT DOCUMENTS

| | | |
|---|---|---|
| 2,516,628 | 7/1950 | Held . |
| 3,827,437 | 8/1974 | Inaba . |
| 3,957,055 | 5/1976 | Linder et al. ................... 128/200.26 |
| 3,964,468 | 6/1976 | Schulz ................................... 128/751 |
| 4,038,987 | 8/1977 | Komiya . |
| 4,043,323 | 8/1977 | Komiya . |
| 4,122,856 | 10/1978 | Mosior et al. . |
| 4,174,715 | 11/1979 | Hasson . |
| 4,467,802 | 8/1984 | Maslanka . |
| 4,646,751 | 3/1987 | Maslanka ........................ 128/321 X |

Primary Examiner—Michael H. Thaler
Attorney, Agent, or Firm—Fleit, Jacobson, Cohn, Price, Holman & Stern

[57] ABSTRACT

A polyolefin sheath for the coiled wire housing for an actuating wire of a medical instrument such as forceps associated with an endoscope or the like. More specifically, the present invention involves the use of a polyolefin sheath for the coiled wire housing and O-ring seal of silicone associated with the forceps and a supporting housing in an endoscope to eliminate migration of contaminants into the forked end of the housing which supports the pivotal forceps and preventing entry of contaminants between the convolutions of the coiled wire housing.

1 Claim, 1 Drawing Sheet

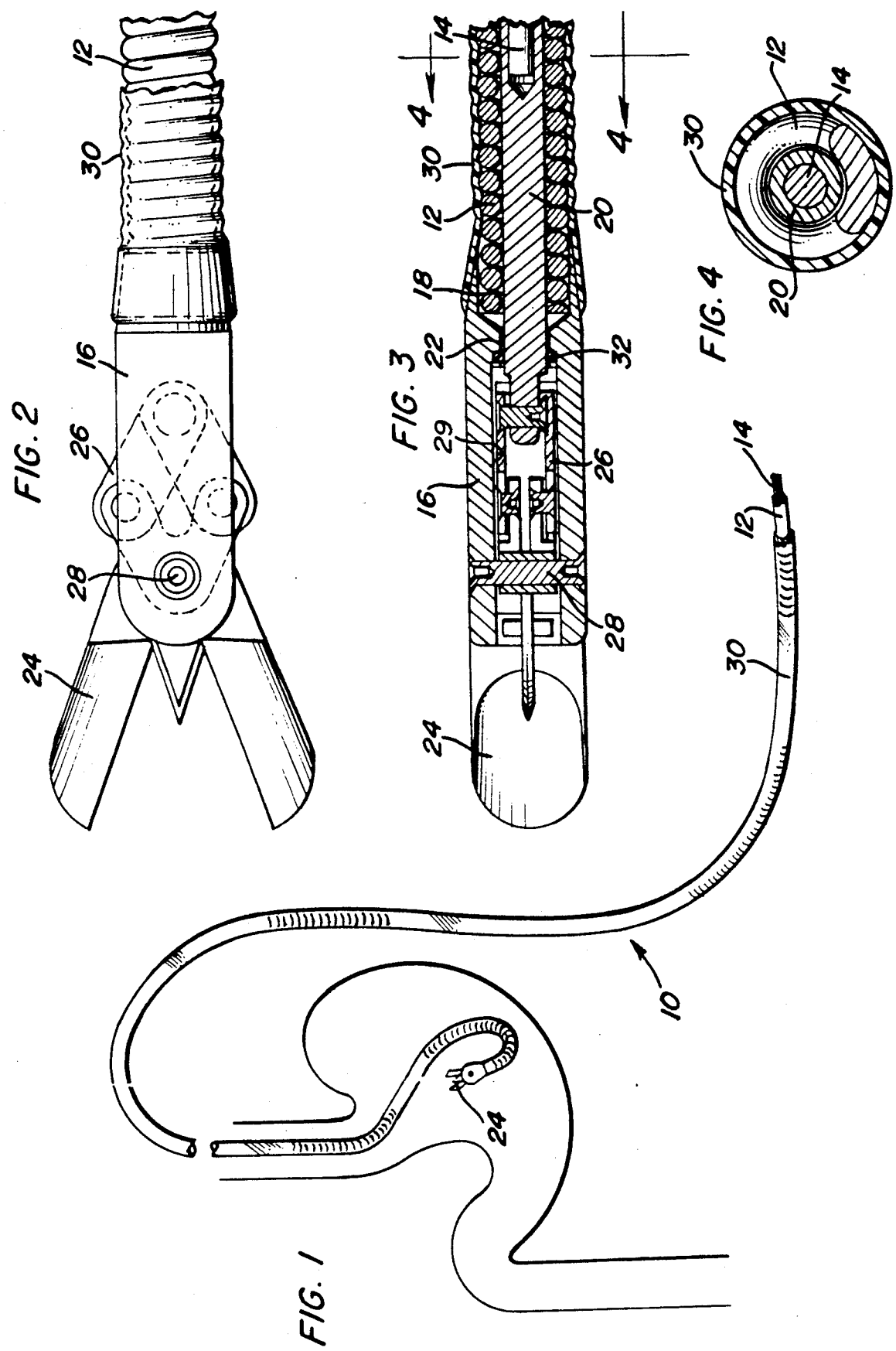

POLYOLEFIN SHEATH AND SILICONE O-RING FOR MEDICAL INSTRUMENT

BACKGROUND OF THE INVENTION

1. Field of the Invention

The present invention generally relates to a polyolefin sheath for the coiled wire housing for an actuating wire of a medical instrument such as forceps associated with an endoscope or the like. More specifically, the present invention involves the use of a polyolefin sheath which is heat shrunk onto the coiled wire housing and an O-ring of silicone associated with the forceps and a supporting housing in an endoscope to eliminate migration of contaminants into the fork or housing which supports the pivotal forceps.

2. Information Disclosure Statement

In the present use of forceps with flexible fiberoptic endoscopes, an elongated coiled wire housing having an internal actuating cable or wire is utilized. The coiled wire housing is flexible and would stretch in the manner of any tight wound spring. The forceps are placed into the suction channel of the endoscope and extended out the end of the instrument when in use for taking a tissue sample. When the operator taking the tissue sample applies suction in order to clear the biopsy site of blood, mucous, gastric contents, feces and the like, the forceps become flooded with this debris. While this debris can be easily cleaned from the outside of the forceps, it is virtually impossible to remove it internally. It has been determined by the Center for Disease Control, that reusable forceps are a definite health hazard for patients being cross-infected as well as a hazard to the staff handling the forceps. Recommendations have been made that steam autoclaving be used but it has been found that denatured protein is still passed on to other patients which results in an immuno compromising infection in certain cases.

The construction of the forceps disclosed in this application is such that blood and debris is prevented from entering the interior of the housing which receives a push rod for operating the forceps and also from entering the coiled wire housing.

The prior art known to applicant does not include any structure equivalent to that in the present invention.

SUMMARY OF THE INVENTION

An object of the present invention is to provide a forceps associated with an endoscope having a channel or passage therein in which a coiled wire housing receiving a central actuating cable is utilized to control the forceps through a push rod received in a forked housing with the forceps also being pivotally supported in the forked housing. The present invention involves the use of a polyolefin shrink tube around the coiled wire housing and a silicone O-ring seal in the housing to exclude blood and other debris from the interior of the housing and wire housing while yet permitting normal operation of the forceps when taking a tissue sample or the like.

Another object of the invention is to provide a polyolefin shield or sheath in accordance with the preceding object in which the polyolefin sheath completely encloses the coiled wire housing and extends completely to and is sealed to the forked housing by heat shrinking and enclosing part of the forked housing and preventing entry of blood and other contaminants into the housing during normal use of the forceps.

A further object of the invention is to provide a polyolefin sheath for the coiled wire housing of an endoscope of the type using forceps and which includes a housing supporting the forceps with the housing being connected to a coiled wire housing that receives a movable actuating wire with the sheath being relatively thin but impervious to blood or other similar liquids with the sheath extending to and joined to the housing and coiled wire housing by heat shrinking with an approved silicone O-ring seal being inserted in the proximal end of the fork housing which seals around the push rod thereby providing a continuous liquid impervious enclosure or shield for the endoscope and forceps.

A further object of the invention is to provide a polyolefin sheath and O-ring seal for an endoscope having forceps on one end thereof which is relatively easy to apply and relatively inexpensive but yet effective for sealing the external surfaces and mechanism for operating the forceps on the end of an endoscope and preventing contaminants from entering the forceps and endoscope.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a fragmental view illustrating schematically an endoscope with portions broken away illustrating the polyolefin shield thereon.

FIG. 2 is a fragmental elevational view of the forceps at the end of an endoscope.

FIG. 3 is a sectional view of the structure of FIG. 2 illustrating further structural details of the forceps on the end of the endoscope.

FIG. 4 is a sectional view taken substantially upon a plane passing along section line 4—4 illustrating the polyolefin sheath and its associated structure.

DESCRIPTION OF THE PREFERRED EMBODIMENT

FIG. 1 illustrates an endoscope with forceps on the end thereof associated with a stomach or other internal cavity of the body in which the forceps are used to obtain a tissue sample for biopsy analysis. The endoscope with forceps is a known medical instrument and may be similar to that disclosed in U.S. Pat. Nos. 4,043,323 and 4,038,987. Basically, the endoscope with forceps is generally designated by reference numeral 10 and includes a coiled wire housing 12 with a control wire 14 slidably disposed therein with the coiled wire housing 12 being soldered or otherwise connected to a fork housing 16 at 18 in FIG. 3 with the control wire 14 being soldered or otherwise connected to a push rod 20 slidable in a passageway 22 in the housing 16. The push rod 20 is connected to a pair of pivotal jaws 24 through linkage 26 with the jaws being pivoted at 28. The jaws 24 and linkage 26 are received in a slot 29 formed in housing 16. All of this structure is conventional and is used in the manner disclosed in the above-mentioned patents with the details of the endoscope not forming a particular part of the present invention except for its association with the protective enclosure.

The coiled wire housing 12 includes and is provided with a polyolefin sheath 30 that completely encloses the coiled wire housing 12 and is sealed to the housing 16 adjacent solder joint 18 by heat shrinking which completely encapsulates the wire housing 12 and distal end of housing 16 with a polyolefin sheath. Also, the housing 16 is provided with an O-ring seal 32 of silicone at the proximal end with the seal 32 engaging the exterior of the push rod 20 thereby preventing entry of contaminating material into the interior of the housing 16. This will eliminate cross-contamination between patients during reuse of the endoscope even when the endoscope has been autoclaved.

Body materials, blood and the like may still enter slot 29 which enables movement of the linkage 26 and jaws 24 but it cannot enter into the passageway 22 due to O-ring seal 32 located just inwardly of slot 29 The polyolefin sheath may be a clear, flexible, radiation cross-linked, heat shrinkable polyolefin tubing and the O-ring seal may be of medical grade silicone material which are approved materials for use in medical instruments and are constructed such that they will not be contaminated by contact with blood or other material when cleaned with normal cleaning procedures, autoclaving and the like with the sheath being relatively thin and on the order of 075". The use of the sheath and O-ring seal will not adversely affect the mechanical operation of the forceps or endoscope but will prevent cross-contamination between patients during reuse of the endoscope which can occur even with autoclaving.

The foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

What is claimed as new is as follows:

1. In combination, an endoscope having forceps on the end thereof which includes a rigid housing having a forked end pivotally supporting a pair of jaws for use in taking tissue samples for analysis, said rigid housing including a cylindrical tubular passage, a push rod closely received in and slidably mounted in said passage, a pair of pivotal links connecting one end of the push rod to said jaws, an elongated actuating wire connected to the other end of said push rod, a flexible coiled wire housing enclosing the actuating wire for the jaws, said rigid housing including a cylindrical cavity extending from the end of the rigid housing inwardly toward the passage and telescopically receiving an end of the coiled wire housing, means connecting the end of the coiled wire housing to the cavity in said rigid housing, a flexible plastic sheath of polyolefin enclosing the coiled wire housing and telescoped over the exterior of the end of the housing having the cavity therein and being sealed to the exterior of the rigid housing and coiled wire housing by heat shrinking, an O-ring seal in said passage in the rigid housing adjacent the forked end in sliding sealed engagement with the periphery of the push rod, said passage including a peripheral groove receiving said O-ring seal, said O-ring seal engaging the exterior of the push rod along a peripheral contact line to prevent entry of contaminants into the space between the push rod and interior of the passage in the rigid housing without substantially increasing the force necessary to be exerted on the actuating wire to actuate the jaws and enabling the endoscope to be reused without cross-contamination of patients after autoclaving.

* * * * *